(12) United States Patent
Huffman (10) Patent No.: US 7,108,507 B2
(45) Date of Patent: Sep. 19, 2006

(54) DENTAL MODEL POURING JIG

(76) Inventor: Ronald E. Huffman, P.O. Box 68440, Oro Valley, AZ (US) 85737

( * ) Notice: Subject to any disclaimer, the term of this patent is extended or adjusted under 35 U.S.C. 154(b) by 257 days.

(21) Appl. No.: 10/215,370

(22) Filed: Aug. 7, 2002

(65) Prior Publication Data

US 2004/0029071 A1    Feb. 12, 2004

(51) Int. Cl.
*A61C 19/00* (2006.01)
(52) U.S. Cl. .......................... 433/53; 433/74
(58) Field of Classification Search .................. 433/74, 433/68, 53, 54, 55, 49, 64, 61, 62
See application file for complete search history.

(56) References Cited

U.S. PATENT DOCUMENTS

| | | | |
|---|---|---|---|
| 2,037,344 A | 4/1936 | Schwartz | |
| 2,234,411 A | 3/1941 | McDonald | |
| 2,376,384 A | 5/1945 | Ringle et al. | |
| 2,577,420 A | 12/1951 | Jablonski et al. | |
| 2,613,440 A | 10/1952 | Murray et al. | |
| 2,669,780 A * | 2/1954 | Mann | 433/53 |
| 3,150,448 A | 9/1964 | Wozar | |
| 3,461,562 A | 8/1969 | Cooper | |
| 3,650,032 A | 3/1972 | Kestler | |
| 3,832,777 A | 9/1974 | Tinder | |
| 3,913,230 A | 10/1975 | Weiss | |
| 4,174,570 A | 11/1979 | Schwartz | |
| 4,229,167 A | 10/1980 | Kikuchi et al. | |
| 4,371,339 A * | 2/1983 | Zeiser | 433/74 |
| 4,403,961 A | 9/1983 | Gurney | |
| 4,436,511 A | 3/1984 | Mitchell, Sr. | |
| 4,504,226 A * | 3/1985 | Gordon | 433/63 |
| 4,865,546 A | 9/1989 | Naylor | |
| 4,886,453 A * | 12/1989 | Ludwigs | 433/54 |
| 5,015,182 A | 5/1991 | Newberry | |
| 5,044,949 A | 9/1991 | Xanthopoulos | |
| 5,586,884 A | 12/1996 | Kraus | |
| 6,033,221 A | 3/2000 | Tsubota et al. | |
| 6,186,781 B1 | 2/2001 | Iba | |

* cited by examiner

*Primary Examiner*—Melba N. Bumgarner
(74) *Attorney, Agent, or Firm*—Merchant & Gould P.C.

(57) ABSTRACT

The dental model pouring jig of the present invention includes a base member that supports a model base support member and a mold support member. The model base support member is secured to the base member and is capable of mounting a dental model base. The mold support member is adjustably secured to the base member and capable of mounting a mold of a person's teeth. The mold support member is adjustable relative to the model base support member to properly position the mold adjacent the dental model base.

20 Claims, 7 Drawing Sheets

DENTAL MODEL POURING JIG

BACKGROUND OF THE INVENTION

1. Field of the Invention

The invention relates to dental models and methods of forming dental models. More particularly, the invention relates to an adjustable dental model pouring jig and a method of using the same.

2. Related Art

Traditional dental model pouring jigs and apparati for creating a dental model from a mold of a person's teeth have been in use for many decades. The model is typically formed by having a patient bite into a pliant casting material, which cures to create a mold cavity having a negative impression of the patient's teeth and gums. The mold can be of all or any portion of the patient's gum line. A castable material is then poured into the negative impression to create a stone replica or dental model of the patient's teeth and gums.

The primary function of a dental pouring jig is to hold the mold of a person's teeth and position pins adjacent the mold when creating a model of the teeth using a model forming (castable) material. In the past, the pins were commonly clipped or temporarily secured to a flat disk that was held in position by features of the pouring jig. More recently, the pin positioned by first drilling a hole into a model of the teeth that has been formed by filling the mold of a person's teeth with a model forming material and then gluing the pin into the hole.

Known pouring jigs have many disadvantages. For example, the adjustment features of known pouring jigs, if available, are typically awkward and difficult to adjust with any degree of precision. Further, typically only the feature holding the mold or the feature holding the pins is adjustable. With this limited adjustability, it is difficult to position the mold and pins in a precise way relative to each other either when preparing to pour a dental model using the pouring jig.

Another disadvantage of known pouring jigs is the amount of time it takes to make adjustments to the jig and the ability to recreate the same adjusted position. Also, known pouring jigs are typically configured for a single mold and dental model base size, such as, for example, sizes that reflect a large, medium and small sized mouths. A yet further limitation of known pouring jigs is that they are configured for either a quadrant or a full arch dental model base, but not compatible for both a quadrant and full arch dental model base.

SUMMARY OF THE INVENTION

The present invention generally relates to dental models and methods and apparati for forming dental models from a mold of a person's teeth. More particularly, the invention relates to adjustable dental model pouring jigs and a method of using the pouring jig to create a dental model from a mold of a person's teeth. The pouring jig includes a base member that supports a model base support member and a mold support member. The model base support member is secured to the base member and is capable of mounting a dental model base. The mold support member is adjustably secured to the base member and capable of mounting a mold of a person's teeth. The mold support member is adjustable relative to the model base support member to properly position a mold of a person's teeth adjacent the dental model base.

In other embodiments, the pouring jig may include a mold support member that is adjustable in two planes relative to a plane of the base member. The base member may include a locking mechanism that fixes the mold support member to the base member in an adjusted position. The mold support member may also include a mold platform that is pivotally secured to the mold support member and configured to mount a mold of a person's teeth. Further, the model base support member may include a first portion secured to the base member and a second portion, pivotally mounted to the first portion, that is configured to mount a model base attachment plate.

The above summary of the present invention is not intended to describe each embodiment or every implementation of the present invention. The Figures and the detailed description that follow more particularly exemplify a preferred embodiment.

BRIEF DESCRIPTION OF THE DRAWINGS

The invention may be more completely understood in consideration of the following detailed description of preferred embodiments of the invention in connection with the accompanying drawings, in which.

While the invention is amenable to various modifications and alternative forms, the specifics thereof have been shown by way of example in the drawings and will be described in detail. It should be understood, however, that the intention is not to limit the invention to the particular embodiment described. On the contrary, the intention is to cover all modifications, equivalents, and alternatives falling with in the spirit and scope of the invention.

DETAILED DESCRIPTION OF THE PREFERRED EMBODIMENT

The present invention is believed to be applicable to a pouring jig used to create a dental model and the method of using the same. In particular, the present invention is directed to a dental model pouring jig that is adjustable in multiple planes and includes features with multiple degrees of freedom. While the present invention may not be so limited, an appreciation of various aspects of the invention will be gained through a discussion of the examples provided below.

Pouring jigs have been used for years to assist in creating a dental model from a mold or impression of a person's teeth. Typically, a pouring jig includes a member mounting a mold of a person's teeth and a member for mounting a dental model base adjacent the mold.

Figure 1:
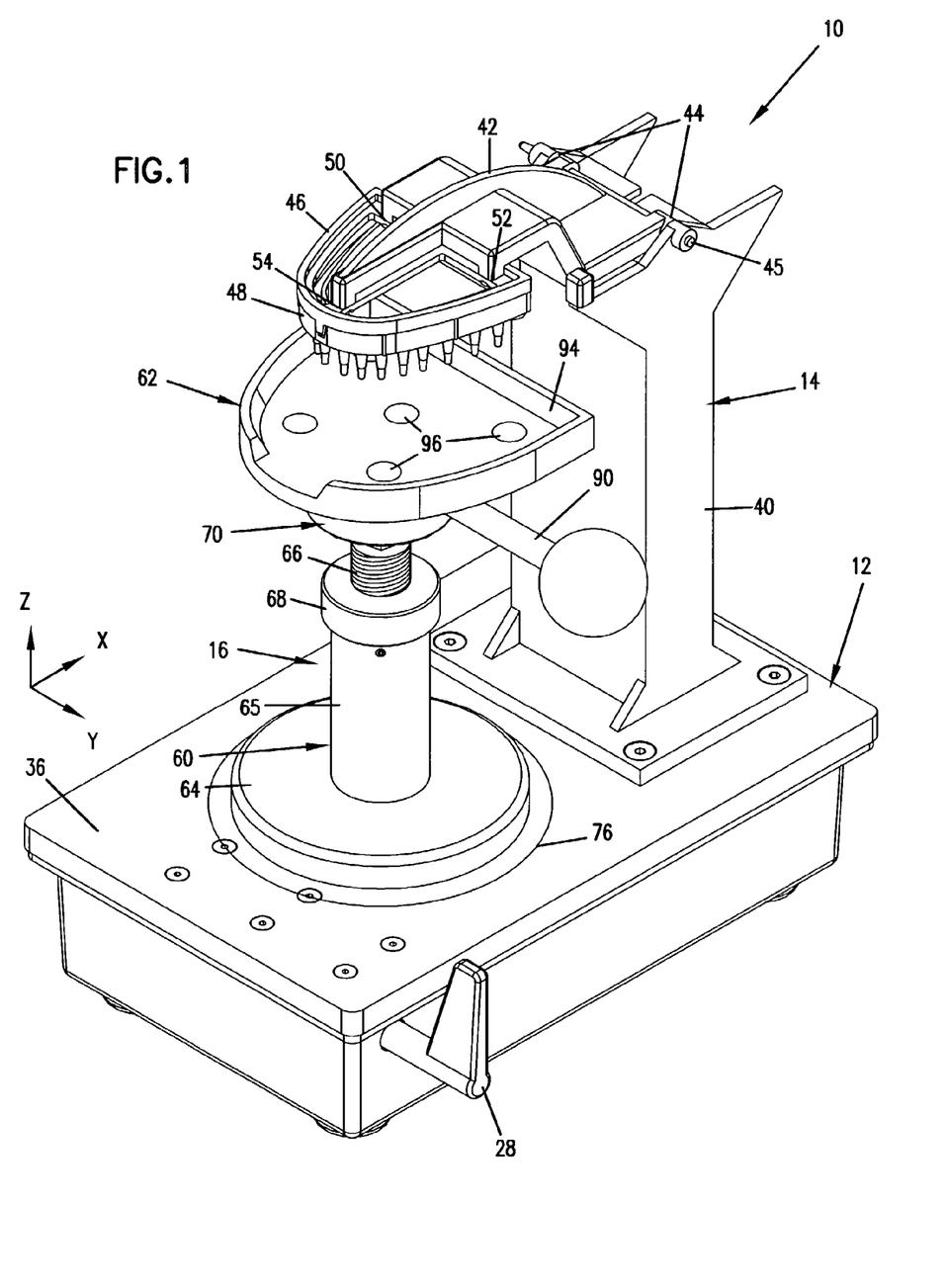
FIG. 1 is a top perspective view of one example of a dental model pouring jig according to the present invention.

FIG. 1 illustrates dental model pouring jig 10 of the present invention. Pouring jig 10 includes a base member 12, a model base support member 14 and a mold support member 16. Model base support member 14 includes a first portion 40 secured to base member 12 and a second portion 42 that is pivotally secured to the first portion at pivot points 44 with a pivot member 45. The mold support member 16 includes a stand portion 60 and a mold platform 62. The stand portion 60 is adjustable in all three of the X, Y, and Z directions. The mold platform 62 is pivotally adjustable relative to the stand portion. Thus, adjustability of the stand portion 60, the mold platform 62, and the pivotal attachment of second portion 42, provides for a dental model pouring jig that is adjustable in multiple directions to facilitate the pouring and creation of a dental model.

Figure 2:
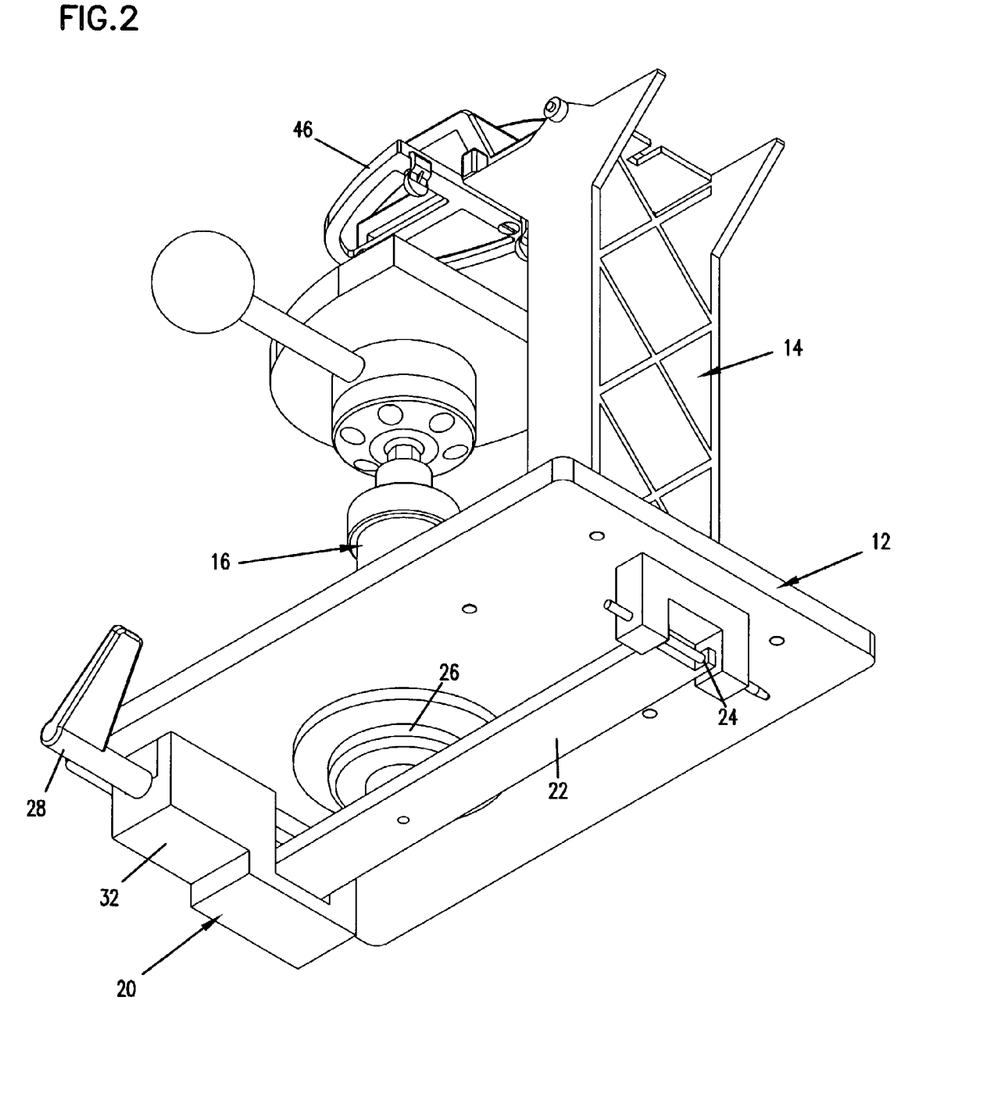
FIG. 2 is a bottom perspective view of the pouring jig of FIG. 1 with a portion of the base member and the dental model base removed.

Referring now to FIG. 2, the features of base member 12 are shown in greater detail. Base member 12 includes a locking mechanism that may be used to lock or hold mold support member 16 in a given X-Y position on a top surface 36 of the base member (see FIG. 1). Locking mechanism 20 includes a pivot member 22, a pivot point 24, a locking portion 26, a lever 28, a cam portion 30 secured to the lever (see FIG. 3), and a lever bracket 32. The pivot member 22 is secured at the pivot point 24 on one end and is engaged by the cam portion 30 of lever 28 near an opposing end. Locking portion 26 is mounted to the pivot member preferably at some point between the pivot point and where the cam portion engages the pivot member. The cam portion 30 preferably engages pivot member 22 at a point as far from pivot point 24 as possible in order to create the greatest amount of leverage for disengaging locking portion 26 from the mold support member 16.

Figure 3:
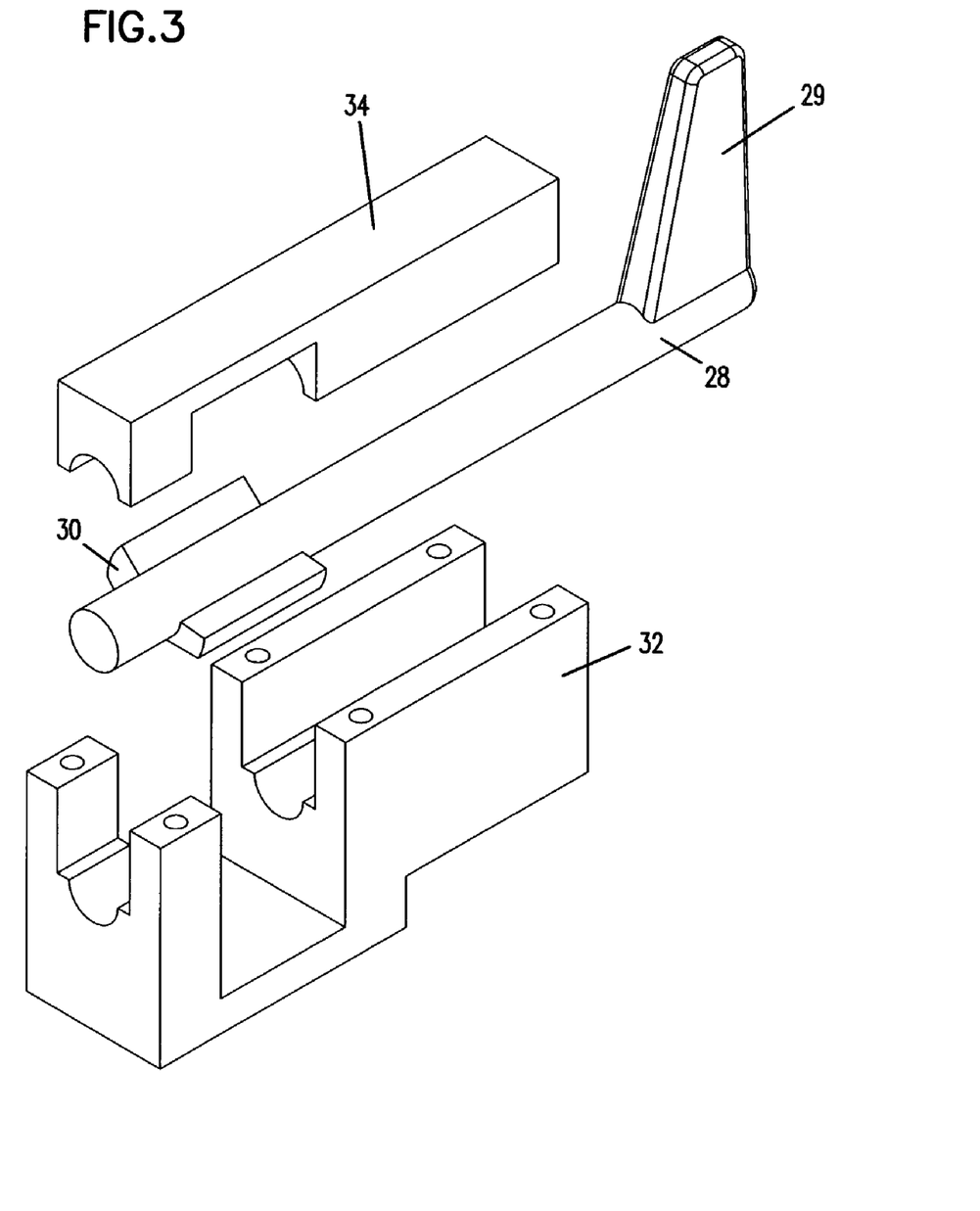
FIG. 3 is an exploded view of a portion of one example of a base member locking mechanism according to the invention.

Referring now to FIG. 3, the lever 28 and lever bracket 32 are shown with greater detail. Cam portion 30 is attached at an end of lever 28 opposite the position of a lever handle 29. Cam portion 30 is configured to include a specific cam surface having a cam surface angle. Cam portion 30 is also configured to restrict the rotation of lever 28 to a predetermined amount of rotation. In this embodiment, the lever handle 29 of the lever is in the upright position when locking portion 26 is in the locked position, and is rotated at about 90 degrees after locking portion 26 is disengaged from the mold support member 16. In other embodiments, the lever may rotate through greater or smaller angles of rotation to engage and disengage the locking portion. FIG. 3 further illustrates a lever bracket cover 34 that captures the lever within the lever bracket 32. In other embodiments, a lever bracket cover may not be required due to the particular lever bracket and lever design.

In this embedment, locking portion 26 is a magnet that is strong enough to hold mold support member 16 in a given X-Y position on top surface 36 of the base member 12. The strength of the magnet should be strong enough to hold the mold support member in a given position to prohibit the inadvertent movement of the mold support member, but allow the locking portion to be easily releasable for adjusting the mold support member.

In other embodiments, locking mechanism 20 may be configured differently, having different components and features for locking the mold support member 16 in a given X-Y position. For example, the locking mechanism 20 may include a ball and socket configuration wherein the ball is secured to the mold support member and the socket portion, when tightened, secures the mold support member to base member 12. Another embodiment of locking mechanism 12 may include a threaded shaft with a nut, wherein tightening the nut tightens the mold support member against the base member at a certain X-Y position.

Referring again to FIG. 1, the model base support member 14 will be described in further detail. The model base support member may also include an attachment plate 46 (see also FIG. 2) to which a dental model base or pin locator 48 may be attached. The attachment plate 46 is secured to second portion 42 at connecting points 50, 52 and 54 with fasteners, adhesives, or the like.

Typically, second portion 42 is configured for a particular attachment plate size. For example, there may be attachment plate sizes for an adult sized mouth (large), a youth sized mouth (medium), and a child sized mouth (small). Therefore, when creating a dental model from the mold or impression of a particular sized mouth, the second portion 42 may be replaced with the appropriate sized second portion by removing pivot member 45 and adding the proper sized second portion with the correct sized attachment plate for the correct sized dental model base or pin locator. In other embodiments, second portion 42 may be permanently fixed to first portion 40 such that an entirely different pouring jig 10 could be used for each of the large, medium or small attachment plate sizes.

An advantage of the model base support member 14 illustrated in FIGS. 1 and 2 is that the second portion 42 may be moved between a first position (shown in FIGS. 1 and 2) that positions the dental model base or pin locator adjacent the mold platform 62, and a second position pivotally removed from the mold platform. In the embedment illustrated in FIGS. 1 and 2, second portion 42 pivots 180 degrees between the first and second positions so that in the second position the attachment plate and dental model base are facing upward rather than the generally downward facing arrangement of the first position. While in the second position, it may be easier to mount the attachment plate at connecting points 50, 52 and 54, and also attach the dental model base or pin locator to the attachment plate when preparing the pouring jig 10 for creating a dental model. Also, when in the second position, it may be easier to arrange pins is the dental model base and prepare the pins for insertion into the mold by, for example, pre-covering the pins with a layer of model forming material to ensure that the pins are properly secured within the model formed from the mold.

A further advantage of the model base support member 14 of the present invention is that it may be compatible with both a quadrant and a full arch attachment plate and dental model base or pin locator. In other embodiments, the connecting points 50, 52 and 54 may be configured differently for mounting different attachment plate designs or for mounting a dental model base directly to the second portion. For example, there may be two, four, or more connecting points depending on the design of the piece which is being connected to the second portion.

The configuration illustrated in FIG. 1 is intended to be compatible with an entire family of attachment plates and dental model base designs and configurations as shown and described in U.S. Pat. Nos. D 429,815, D430,672, D433, 136, D433,754, D444,559, D443,363, D456,904, D457,964, D457,963, D456,903, D457,636, D457,243, D456,902, D457,637, D464,432, D465,027, D464,431, D457,455, D464,732, D469,151, D468,432, D468,018, D481,797, D469,537, 5,788,490, 5,800,166, 5,868,569, 5,934,901, 6,471,513, and 6,884,068, U.S. Patent Publication No. US 2002-0102514 A1, and U.S. patent application Ser. No.09/349,192, which are incorporated herein by reference in their entirety. This family of patents and patent applications relates to, but is not limited to, attachment plates and dental model bases for full and half arch applications that include removable or fixed pins and are capable of attachment to an articulator with ball and socket and snap fit connection features.

The pin locator 48 illustrated in FIG. 1 is comparable in some respects to the dental model base configurations referenced in the above issued U.S. patents and patent applications, in that it is configured to be quickly releasable from the attachment plate and may include a variety of different pin configurations. Pin locator 48 may include relatively long pins (as compared to pins of a dental model base) that extend from the pin locator for improved visual alignment and positioning of the dental mold relative to the pin locator. It is intended that after the mold is properly positioned relative to the pin locator, that the pin locator is replaced with a dental model base prior to forming a dental model from the mold.

Figure 4:
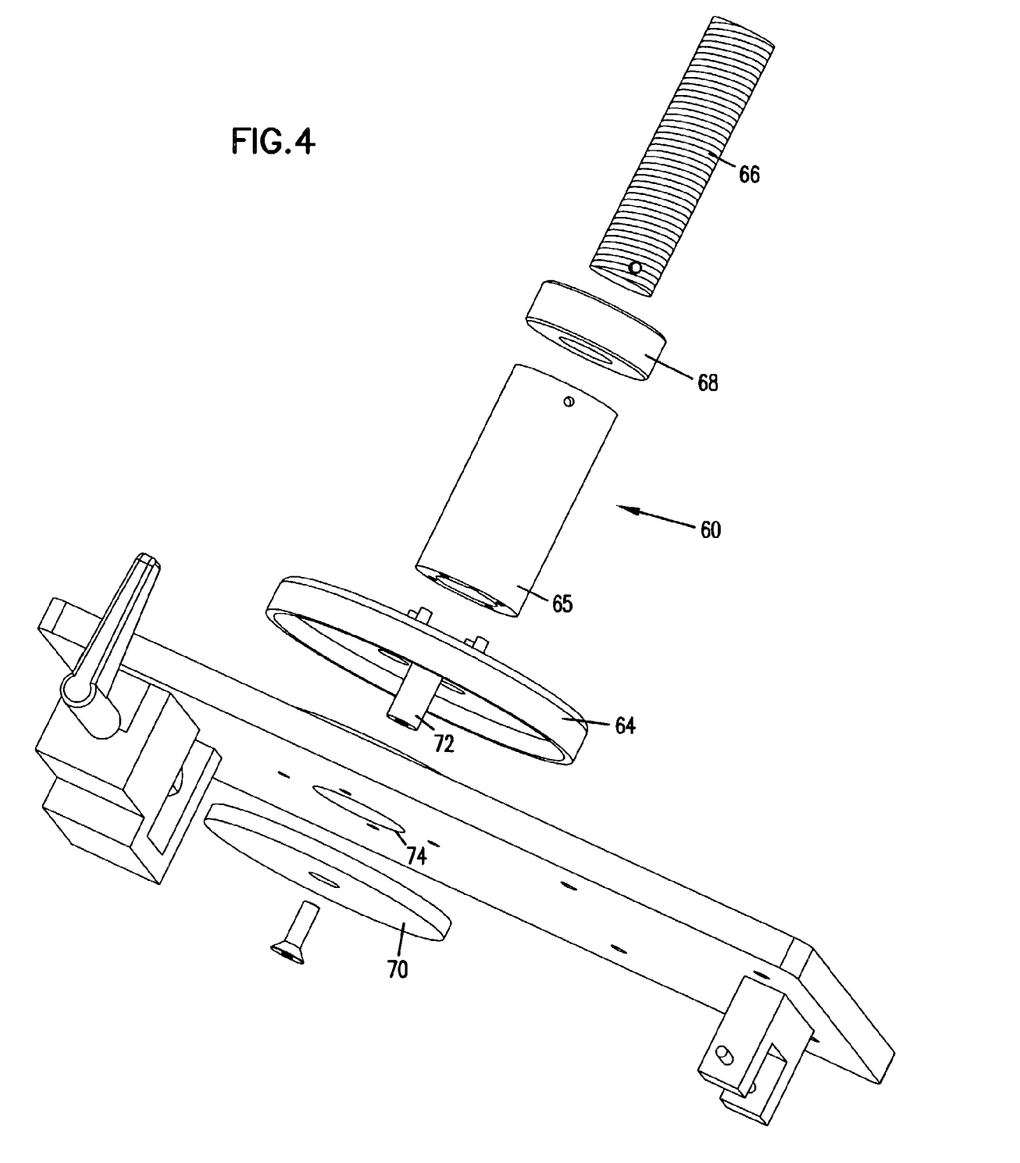
FIG. 4 is an exploded view of one example of a stand portion of the mold support member according to the invention.
Figure 5:
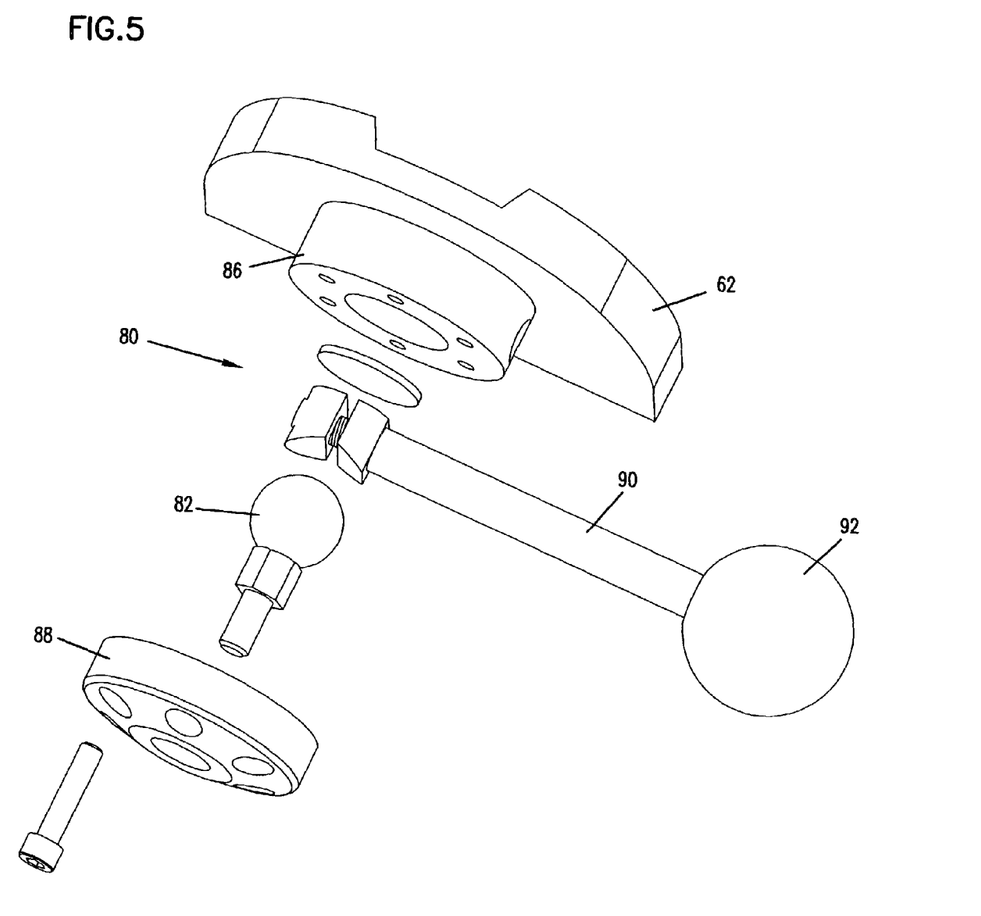
FIG. 5 is an exploded view of one example of a mold platform and mold platform adjuster according to the present invention.

Referring now to FIGS. 1, 4 and 5, the mold support member 16 is described in greater detail. The stand portion 60 of the mold support member includes a stand base 64, a bore portion 65 mounted to the stand base, a threaded shaft 66 insertable into the bore portion, a threaded nut 68 secured to the bore portion that engages the threaded shaft, and an opposing plate 70 positioned adjacent the base member 12 on an opposite side of top surface 36 from the position of stand base 64. The exploded view of FIG. 4 illustrates the relatively positioning of these various features and how they may be assembled.

The threaded nut portion 68 is secured to bore portion 65, but is rotatable relative to the bore portion. The threaded shaft 66 engages the internal threads of the nut such that rotation of the nut moves the thread shaft 66 within bore portion 65. In other embodiments, bore portion includes internal threads, and the threaded shaft engages the threads of the bore portion. In this configuration, the threaded nut portion may not be required to move the threaded shaft relative to the bore portion.

The stand base 64 and opposing plate 70 are secured to each other and configured such that a protrusion 72 extending from the stand base may move within a bore 74 formed in the base member. This arrangement allows the stand portion 60 to move in the X-Y plane relative to base member 12 when locking mechanism 20 has disengaged locking portion 26 from the stand portion 60. When the locking portion 26 engages opposing plate 70, the stand portion 60 is locked or fixed against top surface 36 in a given X-Y position.

To assist in centering and determining the X-Y position of stand portion 60 relative to top surface 36, a groove 76 (see FIG. 1) may be formed in top surface 36 as a reference point.

The stand base 64 is designed in parts to keep debris and other foreign objects from collecting on top surface 36 in the area over which stand base 64 may move in the X-Y plane. The stand base may include an outside ring or wall, as shown in FIG. 4, that engages top surface 36 to prevent the debris or foreign objects from moving under the stand base.

Referring now to FIG. 5, the mold platform 62 and mold platform adjuster 80 are shown in greater detail. The mold platform adjuster includes a ball 82 and socket 84 in a configuration that permits pivotal adjustment of the mold platform 62 relative to stand portion 60 and the model base support member 14. The ball and socket are captured between an upper member 86 and a lower member 88. Socket 84 is adjusted with an adjuster handle 90 to loosen or tighten the socket, thereby loosening or tightening the mold platform adjuster to release the mold platform or fix the mold platform in a given pivotally adjusted position. The adjuster handle 90 may include a grip member 92 or similar feature to assist in rotating adjuster handle 90 to loosen or tighten the socket 84.

Lower member 88 is secured to threaded shaft 66 of the stand portion 60, whereby vertical adjustment of the shaft portion also vertically adjusts the position of the mold platform and mold platform adjuster.

In other embodiments, the mold platform adjuster 80 may be configured differently while performing the same or similar function. For example, the adjuster may include a ball, such as ball 82, and a set screw that is inserted through the upper or lower member to lock the mold platform in a given pivotally adjusted position. In a further embodiment, the mold platform may be hinged to the stand portion so that it is adjustable in a single direction such as, for example, the arrangement of the first and second portions of the model base support member. In yet another embodiment, the adjuster may include two or more separate hinges wherein each hinge may be separately locked to hold the platform in a given hinged position, thereby allowing the platform to be adjusted in multiple directions.

Figure 6:
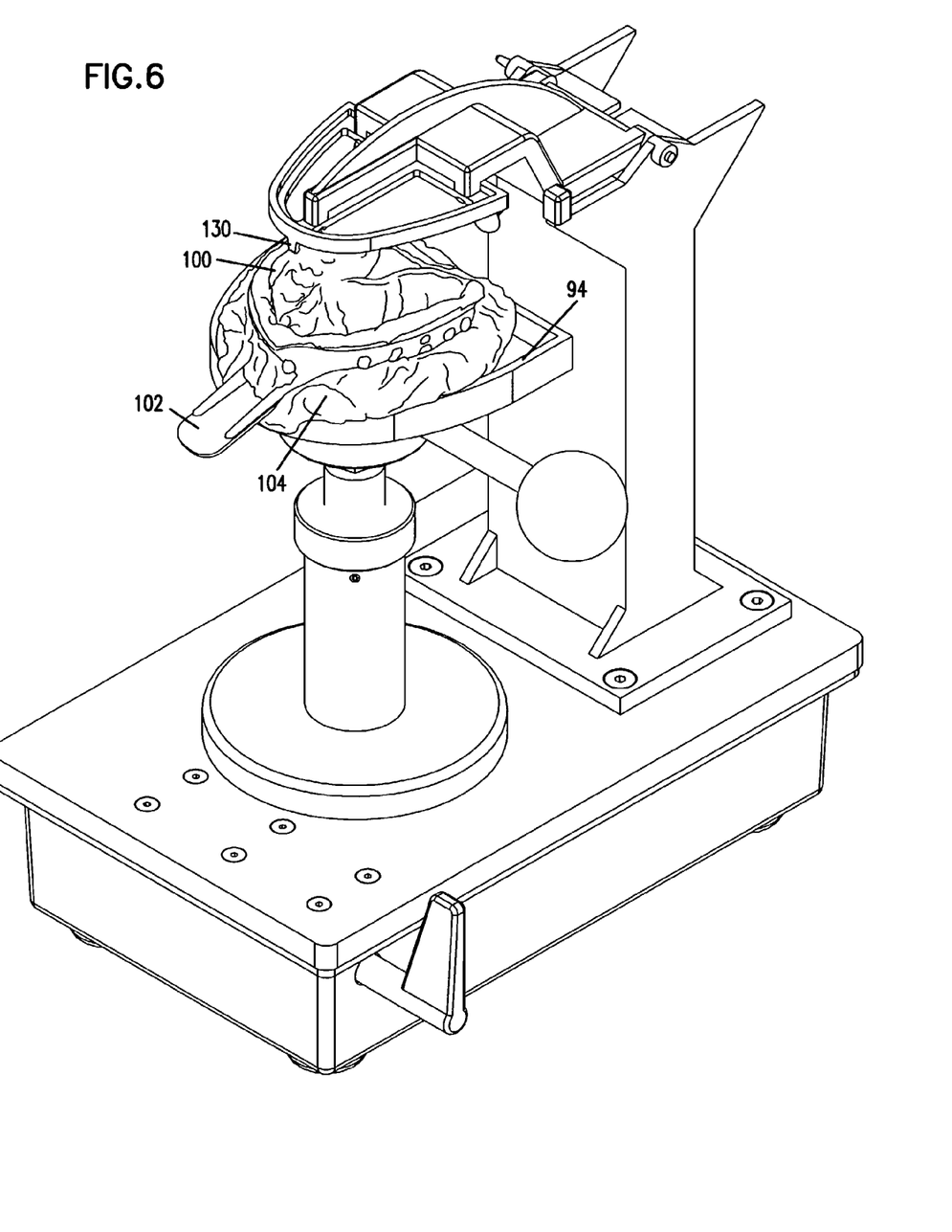
FIG. 6 is a top perspective view of one example of a dental model pouring jig according to the invention having a mold of a person's teeth mounted to the pouring jig.

The mold platform 62 is configured to mount a mold or impression of a person's teeth 100 as shown in FIG. 6. To assist in positioning the mold in a particular position on the platform, the platform may include a raised lip 94 that extends around a portion of the platform. In the configuration of FIG. 6, the raised edge extends around a majority of the platform while leaving a space open for a handle 102 or other feature that extends from the mold for handling the mold. The platform may also include divots or grooves 96 (see FIG. 1) positioned at various places on a top surface of the platform that assist in positioning of the mold. Typically, the platform top surface is covered with a layer of plaster 104 or other impressionable material that the mold is pressed against to form a negative impression of an under side of the mold so that the mold can be replaced in the exact same position each time it is mounted onto the platform. The divots 96 ensure that the material into which the negative impression of the mold is formed maintains a constant position on the platform top surface.

The various components of pouring jig 10 may be made of a variety of different materials. For example, a majority of the components associated with the base member 12, dental model support member 14, and mold support member 16 may be made of metal, metal alloy, polymer-based material, or a reinforced polymer-based material such as, for example, fiberglass-reinforced plastic.

One embodiment of pin locator 48 is further illustrated with reference to FIGS. 7 and 8 (a full arch design). A half arch pin locator design would include the same or similar features described below. Pin locator 48 may include a body portion 110 having a first major surface 112, a second major surface 113, and internal wall 114, and external wall 116, a first end 118, a second end 120, and elongated pins 122 extending from the first major surface. The pin locator may also be configured with ball and socket attachment features 124 and 126 at one end of the body portion and a latch attachment feature 128 at an opposite end of the body portion from the ball and socket features.

The arrangement of the internal and external walls of the body portion relative to the second major surface may create a cavity 130. The volume of the cavity may vary depending on the thickness of the walls, their spacing from each other, and the distance the walls extend from the second major surface. Preferably, the walls are as thin as possible while maintaining necessary structural rigidity. In some embodiments, holes may be formed in the body portion that extend between the first and second major surface that are sized to receive removable locator pins that extend into the cavity. There may be a plurality of holes that each represents a possible tooth location in a dental mold. Thus, the locator pins may be inserted in the body portion in positions that represent tooth locations, and then similarly positioned holes could be used for pins in a dental model base that is used in conjunction with the pin locator.

In a further pin locator embodiment, support protrusions are formed in the cavity that extend from the second major surface. These protrusions may include axially aligned bores that are aligned with holes formed between the first and second major surfaces of the body portion. The protrusions would be configured to support the locator pins. In another embodiment, the protrusions are configured to receive tapered locator pins.

Figure 7:
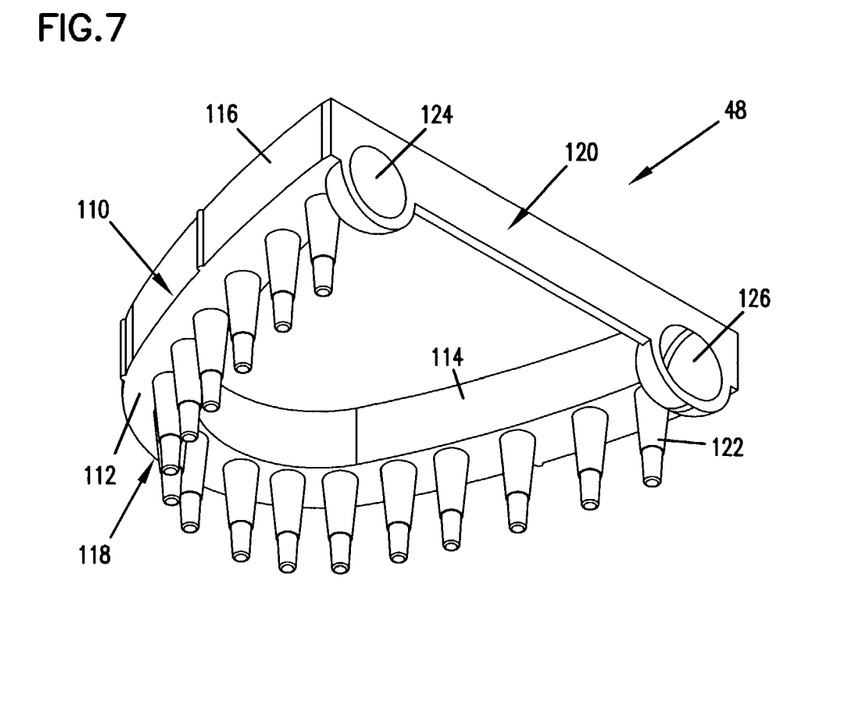
FIG. 7 is a bottom perspective view of the pin locator shown in FIG. 1.
Figure 8:
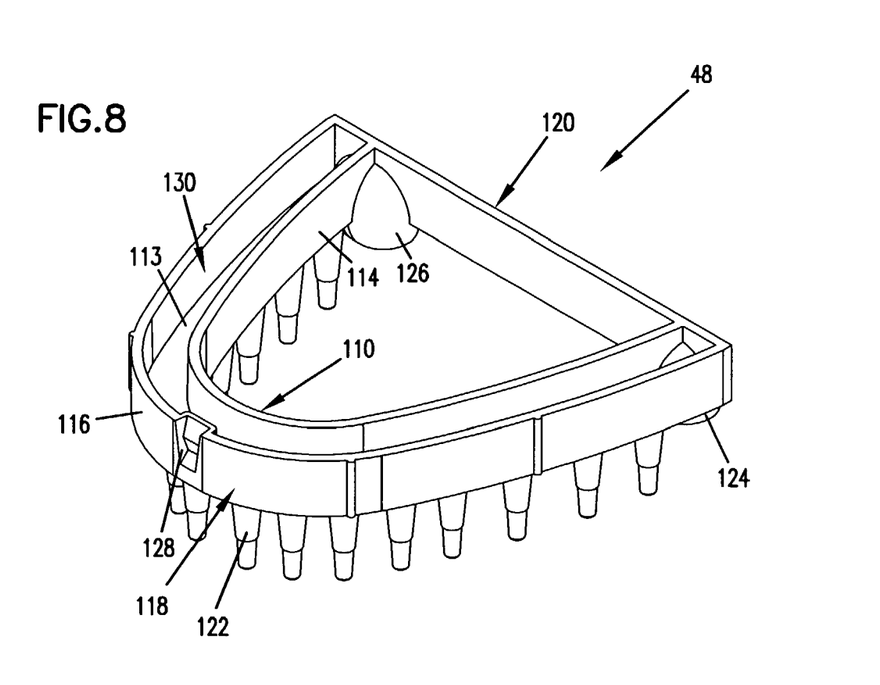
FIG. 8 is a top perspective view of the pin locator shown in FIG. 1.

The locator pins 122 shown in FIGS. 1, 7 and 8 are only exemplary embodiments and should not be construed as limiting the pin designs to what is shown. In other embodiments, the pins may have parallel sidewalls rather than the angled sidewalls shown. The locator pins may also include two or more parts that are secured together to form a single locator pin, wherein each part has a different intended purpose and benefit. The locator pins may be secured to the body portion in several different ways, including, for example, adhering the pins to the first major surface, integrally forming the pins into the body portion, or inserting the pins into holes formed in the body portion (as described above).

The ball and socket attachment features 124 and 126 are, in this embodiment, concave recesses or sockets that are configured to engage a ball feature that releasably secures the ball and socket together. An example of a ball feature is shown in FIGS. 2 and 6 as part of the attachment plate 46. In some embodiments of the present invention, the ball feature may be integrated into the pin locator and the socket feature may be integrated into the attachment plate. When the ball and socket features of the attachment plate and pin locator engage one another, they may be held together in part by latch feature 128 on the pin locator that cooperates with an associated latch feature 130 on the attachment plate (see FIG. 6) in a snap-fit connection. A similar snap-fit connection may be made between the attachment plate and a dental model base. Latch features 128 and 130 may, in other embodiments, be interchangeable between the pin locator and attachment plate. Although the latch features and ball and socket features of the pin locator and attachment plate are formed at generally first and second ends of the pin locator and attachment plate, these features could be located along the side or on the top or bottom of those parts, while providing a similar easy-to-use and adjust apparatus.

In addition to using the pin locator described above in connection with the pouring jig 10 described herein, the pin locator could be adapted for use with other pouring jig configurations and other appropriate dental-related applications. The pin locator and the dental model base that is used in conjunction with the pouring jig of the present invention may have different sizes, for example, small, medium and large sizes that generally match the arch sizes of children, youth and adults, respectively. The pin locator and dental model base may also be configured to represent an upper or lower arch of a person's mouth. The pin locator may be made of a variety of different materials, such as, for example, various polymer-based material such as nylon, polycarbonate plastics, or other castable or injection moldable materials. Preferably, the pin locator is made of a material that is strong, rigid, and light weight, and may, in some embodiments, match the material used for the family of products based on the patents and patent applications listed above.

One example of a method for forming a dental model using a dental model pouring jig according to the present invention includes providing a mold of a person's teeth, mounting the mold to a mold support member, mounting a dental model base to a model base support member, adjusting the mold support member relative to a base member, and adjusting the mold support member relative to the model base support member. The mold is then filled with a model forming material, the dental model base is positioned to engage the model forming material, the model forming material is cured, and the mold is separated from the model forming material.

A more detailed description of one possible method of forming a dental model using the dental model pouring jig of the present invention is described below. The steps described below are not required to be performed in exact order listed and may be replaced with more or fewer step that may accomplish the intended purpose of the invention.

First, the correct attachment plate and second portion of the model base support member size is chosen for a given mold size. In order to change the second portion of a model base support member, the pivot pin is removed and the proper sized second portion is mounted to the model base support member. The second portion with the attachment plate attached is then moved to the first position above the mold support member.

Next, the mold support member is centered below the attachment plate and the mold platform is leveled. The pin locator is attached to the attachment plate and the dental mold is then placed on the mold platform. The pin locator is intended to duplicate all of the relative locations and dimensions of the model base, including pins that may be mounted to the model base. The height of the model platform is adjusted so that the pins in the pin locator do not interfere with the mold, and the mold is positioned so that it is roughly aligned the pins of the pin locator.

At this point, the second portion of the model base support member is rotated to the second position and the mold is removed from the mold platform. Next, plaster or other formable material is applied to the top of the mold platform and a thin layer of plastic film or a like material is placed over the formable material. The mold is pressed down into the formable material to create a negative impression that will allow the mold to be removed from the mold platform and replaced on the platform in the same position. The second portion of the model base support member is then pivoted back into the first position to position the pin locator above the mold. The mold platform adjuster, threaded nut, and locking mechanism are then adjusted to position the mold relative to the pins of the pin locator so that the tips of the pins are within about 0.25 inches vertically of the tooth margins of the mold and as close as possible to the center of each tooth. Due to the quick release and easy adjustment features of the dental model pouring jig of the present invention, the adjustments to place the mold in a proper position is made easier and may be quickly performed.

Once the proper position is established and the dental mold is trimmed and prepared for pouring the dental model, the pin locator and second portion of the model base support member are pivoted into the second position, and the pin locator is removed and replaced with the dental model base. The second portion with dental model base is then brought back into the first position for a final check to ensure proper alignment of the pins of the dental model base relative to the teeth impressions in the mold. The second portion is again rotated into the second position, the mold removed from the mold platform and the dye material (casting or model forming material) is then poured into the dental mold and returned to the mold platform. While the dye material is still in a plastic form, the second portion is rotated to the first position, bringing the dental model base into its final position adjacent the mold with the pins of the dental model base extending into the dye material.

After the dye material has hardened sufficiently, the dental mold and dental model base are removed from the pouring jig. The model base and hardened dye material are moved from the mold, and the dental model has essentially been created.

In other methods of using the present invention, the pouring jig may be used with a dental model base that has no pins and no predrilled holes. With the dental model base properly aligned relative to a dental mold on the pouring jig, a marking apparatus is used to mark the dental model base at locations that represent aligned positions between the dental model base and the teeth impressions in the dental mold. The holes may then be drilled in the dental model base at each of the marks and pins inserted in the holes that are aligned with the teeth impressions.

Various directions of motion and adjustment are described herein with reference to the adjustability of various features and parts of the present invention. A "direction of motion" as used herein may be broadly defined to include several different types of motion, such as, for example, rotational motion, translational motion, and pivotal motion, and movement in all directions within that type of motion. For example, there is translational motion in the X, Y and Z axial directions as well as translational motion in each of the XY, XZ, and YZ planes. Rotational motion can also be defined within the context of an XYZ coordinate system. Pivotal motion, although closely related to rotational motion, may be useful in describing the motion of some features of the present invention, such as the pivotal motion of platform 62 about a single point defined by the ball and socket connection of the platform to the stand 60. Although motion can be defined in more complex ways, the above describe directions of motion define the directions of motion primarily used by the features of the present invention.

The various adjustment features of the present invention could be rearranged in alternative embodiments to provide adjustability in different ways than that shown in the Figures. For example, the ball and socket pivot motion of platform 62 relative to stand 60 could be implemented into the model support member. In another example, the magnetic adjustment mechanism, in a revised configuration, could be implemented into the model support member or the mold support member to permit adjustments of those members in various directions of motion. Thus, the embodiment illustrated in the Figures and described herein is only one example of the many different embodiments that may be realized using the adjustment features disclosed herein to provide a pouring jig with quick and easy adjustability in multiple directions of motion.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A dental model pouring jig, comprising;
   a base member;
   a model base support member secured to the base member and capable of mounting a dental model base;
   a mold support member adjustably secured to the base member; and
   a mold platform coupled to the mold support member and capable of mounting a mold of a person's teeth, the mold support member being vertically adjustable relative to the model base support member to change a position of the mold platform relative to the model base support member;
   wherein the base member comprises a locking mechanism that fixes the mold support member to the base member in an adjusted position, the locking mechanism comprising a magnet that acts upon a portion of the mold support member, and the locking mechanism further comprising a pivot member secured to the magnet and a lever portion that engages the pivot member to move the pivot member about a pivot point, thereby adjusting a position of the magnet.

2. The pouring jig of claim 1 wherein the mold support member is adjustable in two planes relative to a plane of the base member.

3. The pouring jig of claim 1 wherein the lever portion is accessible on an outside portion of the base member.

4. The pouring jig of claim 1 wherein the mold platform comprises a raised portion positioned around a circumference of the platform.

5. The pouring jig of claim 1 wherein the mold platform is pivotally secured to the mold support member and movable about a pivot point, the mold platform capable of being fixed in a given pivoted position.

6. The pouring jig of claim 5 wherein the mold platform is adjustably secured to the mold support member with a ball and socket configuration, and the mold platform is fixed in a given pivoted position by tightening the socket portion about the ball portion.

7. The pouring jig of claim 1 wherein the mold support member comprises a threaded shaft portion and a threaded bore portion, and the threaded shaft is rotatable within the threaded bore to vertically adjust the position of the mold platform.

8. The pouring jig of claim 1 wherein the model base support member is capable of mounting a model base attachment plate that is configured to removably mount a dental model base.

9. The pouring jig of claim 1 wherein the model base support member comprises a first portion secured to the base member, and a second portion configured to mount a dental model base, the second portion being secured to the first portion and capable of moving between first and second positions relative to the mold support member.

10. The pouring jig of claim 9 wherein in the first position, a mounting surface of the first portion of the model base support member faces generally downwards towards the mold support member, and in the second position, the mounting surface of the first portion faces away from the mold support member.

11. The pouring jig of claim 9 wherein the second portion is pivotally secured to the first portion.

12. A dental model pouring jig assembly, comprising;
a base member defining a mounting surface and including a locking mechanism, the locking mechanism comprising a pivot member, a locking portion secured to the pivot member, and a lever engaging the pivot member;
a model base support member comprising a first portion secured to the mounting surface of the base member, and a second portion pivotally secured to the first portion and capable of mounting a dental model base that is configured for mounting a model formed from a, mold of a person's teeth, the second portion being movable between a first position and a second position; and
a mold support member comprising a stand portion adjustably secured to the mounting surface of the base member, and a mold platform capable of mounting a mold of a person's teeth, the mold platform being pivotally adjustable relative to the stand portion and vertically adjustable relative to the base member;
whereby the locking mechanism is configured to adjustably secure the mold support member to the mourning surface of the base member.

13. The pouring jig assembly of claim 12, wherein the locking mechanism is at least partially positioned vertically below the mounting surface of the base member.

14. A dental model pouring jig assembly, comprising;
a dental model base configured to support a model of a plurality of teeth;
a mold formed from a plurality of teeth;
a base member defining a mounting surface;
a model base support member secured to the mounting surface of the base member, wherein the model base support member is configured for mounting the dental model base;
a mold support member adjustably secured to the mounting surface of the base member and configured to mount the mold, the mold support member being adjustable relative to the model base support member to change a position of the mold relative to the model base; and
an attachment plate coupled between the dental model base and the model base support member, the attachment plate including a ball portion and a latching portion that engage a socket portion and a latch portion, respectively, that are defined in opposing ends of the dental model base.

15. The pouring jig assembly of claim 14, further comprising a pin locator configured for mounting to the model base support member, wherein the dental model base is interchangeable with the pin locator.

16. The pouring jig assembly of claim 15, wherein the pin locator includes a plurality of tapered pins configured for alignment with individual teeth in the mold.

17. A dental model pouring jig, comprising;
a base member including a locking mechanism, the locking mechanism including a magnet, a pivot member, and a lever portion that engages the pivot member to move the pivot member about a pivot point, thereby adjusting a position of the pivot point;
a model base support member secured to the base member and capable of mounting a dental model base;
a mold support member adjustably secured to the base member and capable of mounting a mold of a person's teeth, the mold support member being adjustable relative to the model base support member to effectively position the mold adjacent the dental model base;
wherein the locking mechanism the magnet acts upon a portion of the mold support member to fix the mold support member to the base member in an adjusted position.

18. The pouring jig of claim 17 wherein the lever portion is accessible on an outside portion of the base member.

19. A dental model pouring jig assembly, comprising;
a dental model base configured to support a model of a plurality of teeth;
a mold fanned from a plurality of teeth;
a base member defining a mounting surface;
a model base support member secured to the mounting surface of the base member, wherein the model base support member is configured for mounting the dental model base;
a mold support member adjustably secured to the mounting surface of the base member and configured to mount the mold, the mold support member being adjustable relative to the model base support member to change a position of the mold relative to the model base; and
a pin locator configured for mounting to the model base support member, wherein the dental model base is interchangeable with the pin locator.

20. The pouring jig assembly of claim 19, wherein the pin locator includes a plurality of tapered pins configured for alignment with individual teeth in the mold.

* * * * *

UNITED STATES PATENT AND TRADEMARK OFFICE
CERTIFICATE OF CORRECTION

PATENT NO. : 7,108,507 B2  Page 1 of 5
APPLICATION NO. :10/215370
DATED : September 19, 2006
INVENTOR(S) : Huffman It is certified that error appears in the above-identified patent and that said Letters Patent is hereby corrected as shown below:

Front page drawing: Delete front page drawing and replace with the following drawing:

(12) United States Patent
Huffman (10) Patent No.: US 7,108,507 B2
(45) Date of Patent: Sep. 19, 2006

(54) DENTAL MODEL POURING JIG (76) Inventor: Ronald E. Huffman, P.O. Box 68440, Oro Valley, AZ (US) 85737

(*) Notice: Subject to any disclaimer, the term of this patent is extended or adjusted under 35 U.S.C. 154(b) by 257 days.

(21) Appl. No.: 10/215,370

(22) Filed: Aug. 7, 2002

(65) Prior Publication Data
US 2004/0029071 A1 Feb. 12, 2004

(51) Int. Cl.
A61C 19/00 (2006.01)
(52) U.S. Cl. .................................. 433/53; 433/74
(58) Field of Classification Search ............ 433/74, 433/68, 53, 54, 55, 49, 64, 61, 62
See application file for complete search history.

(56) References Cited

U.S. PATENT DOCUMENTS

| | | | |
|---|---|---|---|
| 2,037,344 A | 4/1936 | Schwartz | |
| 2,234,411 A | 3/1941 | McDonald | |
| 2,376,384 A | 5/1945 | Ringle et al. | |
| 2,577,420 A | 12/1951 | Jablonski et al. | |
| 2,613,440 A | 10/1952 | Murray et al. | |
| 2,669,780 A * | 2/1954 | Mann | 433/53 |
| 3,150,448 A | 9/1964 | Wozar | |
| 3,461,562 A | 8/1969 | Cooper | |
| 3,650,032 A | 3/1972 | Kestler | |
| 3,832,777 A | 9/1974 | Tinder | |
| 3,913,230 A | 10/1975 | Weiss | |
| 4,174,570 A | 11/1979 | Schwartz | |
| 4,229,167 A | 10/1980 | Kikuchi et al. | |
| 4,371,339 A * | 2/1983 | Zeiser | 433/74 |
| 4,403,961 A | 9/1983 | Gurney | |
| 4,436,511 A | 3/1984 | Mitchell, Sr. | |
| 4,504,226 A * | 3/1985 | Gordon | 433/63 |
| 4,865,546 A | 9/1989 | Naylor | |
| 4,886,453 A * | 12/1989 | Ludwigs | 433/54 |
| 5,015,182 A | 5/1991 | Newberry | |
| 5,044,949 A | 9/1991 | Xanthopoulos | |
| 5,586,884 A | 12/1996 | Kraus | |
| 6,033,221 A | 3/2000 | Tsubota et al. | |
| 6,186,781 B1 | 2/2001 | Iba | |

* cited by examiner

Primary Examiner—Melba N. Bumgarner
(74) Attorney, Agent, or Firm—Merchant & Gould P.C.

(57) ABSTRACT

The dental model pouring jig of the present invention includes a base member that supports a model base support member and a mold support member. The model base support member is secured to the base member and is capable of mounting a dental model base. The mold support member is adjustably secured to the base member and capable of mounting a mold of a person's teeth. The mold support member is adjustable relative to the model base support member to properly position the mold adjacent the dental model base.

20 Claims, 7 Drawing Sheets

UNITED STATES PATENT AND TRADEMARK OFFICE
CERTIFICATE OF CORRECTION

PATENT NO. : 7,108,507 B2 Page 3 of 5
APPLICATION NO. : 10/215370
DATED : September 19, 2006
INVENTOR(S) : Huffman It is certified that error appears in the above-identified patent and that said Letters Patent is hereby corrected as shown below:

Drawings, Sheet 1 of 7: Delete Sheet 1 of 7 and replace with the following drawing:

UNITED STATES PATENT AND TRADEMARK OFFICE
CERTIFICATE OF CORRECTION

PATENT NO. : 7,108,507 B2  Page 4 of 5
APPLICATION NO. : 10/215370
DATED : September 19, 2006
INVENTOR(S) : Huffman It is certified that error appears in the above-identified patent and that said Letters Patent is hereby corrected as shown below:

Drawings, Sheet 5 of 7: Delete sheet 5 of 7 and replace with the following drawing:

UNITED STATES PATENT AND TRADEMARK OFFICE
CERTIFICATE OF CORRECTION

PATENT NO. : 7,108,507 B2
APPLICATION NO. : 10/215370
DATED : September 19, 2006
INVENTOR(S) : Huffman It is certified that error appears in the above-identified patent and that said Letters Patent is hereby corrected as shown below:

Col. 11, line 21, claim 12: "support member to the mouring" should read --support member to the mounting--

Signed and Sealed this

Fourth Day of March, 2008

JON W. DUDAS
*Director of the United States Patent and Trademark Office*